US008946472B2

(12) United States Patent
Berti et al.

(10) Patent No.: US 8,946,472 B2
(45) Date of Patent: Feb. 3, 2015

(54) BIO-BASED TEREPHTHALATE POLYESTERS

(75) Inventors: Corrado Berti, Lugo (IT); Enrico Binassi, Bologna (IT); Martino Colonna, Bologna (IT); Maurizio Fiorini, Bologna (IT); Ganesh Kannan, Evansville, IN (US); Sreepadaraj Karanam, Bergen op Zoom (NL); Marzia Mazzacurati, Bologna (IT); Ihab Odeh, Valenica, CA (US)

(73) Assignee: Sabic Innovative Plastics IP B.V. (NL)

( * ) Notice: Subject to any disclaimer, the term of this patent is extended or adjusted under 35 U.S.C. 154(b) by 377 days.

(21) Appl. No.: 12/347,337

(22) Filed: Dec. 31, 2008

(65) Prior Publication Data
US 2010/0168372 A1 Jul. 1, 2010

(51) Int. Cl.
  *C07C 5/367* (2006.01)
  *C07C 51/265* (2006.01)
  *C07C 67/08* (2006.01)
  *C08G 63/78* (2006.01)
  *C08G 63/183* (2006.01)

(52) U.S. Cl.
  CPC ............... *C08G 63/78* (2013.01); *C07C 5/367* (2013.01); *C07C 51/265* (2013.01); *C07C 67/08* (2013.01); *C08G 63/183* (2013.01)
  USPC ........................... 562/480; 562/408; 562/409

(58) Field of Classification Search
  CPC ...... C07C 5/367; C07C 51/265; C07C 67/08; C07G 63/183; C07G 63/78
  USPC .......................................... 562/408, 409, 480
  See application file for complete search history.

(56) References Cited

U.S. PATENT DOCUMENTS

| 4,382,152 | A  | 5/1983  | Wideman et al. |
| 4,837,347 | A  | 6/1989  | Rashkin |
| 5,998,525 | A  | 12/1999 | Wang et al. |
| 6,187,569 | B1 | 2/2001  | Bramucci et al. |
| 6,500,890 | B2 | 12/2002 | Edwards et al. |
| 6,723,873 | B1 | 4/2004  | Murdoch |
| 6,919,489 | B1 | 7/2005  | McCusker-Orth |
| 6,927,275 | B2 | 8/2005  | Hirokane et al. |
| 7,385,081 | B1 | 6/2008  | Gong |
| 2006/0135668 | A1 | 6/2006 | Hayes |
| 2006/0135734 | A1 | 6/2006 | Kurian |
| 2008/0025903 | A1 | 1/2008 | Cortright |
| 2008/0103340 | A1 | 5/2008 | Binder et al. |
| 2008/0275277 | A1 | 11/2008 | Kalagias |
| 2009/0246430 | A1 | 10/2009 | Kriegel et al. |
| 2010/0028512 | A1 | 2/2010 | Kriegel et al. |
| 2010/0168371 | A1 | 7/2010 | Berti et al. |
| 2010/0168372 | A1 | 7/2010 | Berti et al. |
| 2010/0168373 | A1 | 7/2010 | Berti et al. |
| 2010/0168461 | A1 | 7/2010 | Berti et al. |
| 2011/0262669 | A1 | 10/2011 | Kriegel et al. |

FOREIGN PATENT DOCUMENTS

| EP | 0086296 A1 | 9/1985 |
| EP | 0522839 | 1/1993 |
| EP | 1674551 A1 | 6/2006 |
| EP | 1842868 | 10/2007 |
| EP | 1882712 A1 | 1/2008 |
| GB | 789809 | 1/1958 |
| GB | 974068 | 11/1964 |
| JP | 2000212109 | 2/2000 |
| WO | 2007027832 A2 | 3/2007 |
| WO | 2007089600 | 8/2007 |
| WO | 2008057220 A2 | 5/2008 |
| WO | 2008154600 | 12/2008 |
| WO | 2009059253 A2 | 5/2009 |
| WO | 2009059254 A2 | 5/2009 |
| WO | 2009063174 | 5/2009 |
| WO | 2009063176 A1 | 5/2009 |
| WO | 2009079213 | 6/2009 |
| WO | 2009120457 | 10/2009 |

OTHER PUBLICATIONS

Akiyoshi et al; Abstract of: Kyushu Daigaku Kogaku Iho, 1951, 24, 75-77.*
Schwanert H: "Ueber Terephtalsaure und Camphresinsaure" Liebigs Annalen Der Chemie Unk Pharmacie, vol. 132, No. 3, 1864, pp. 257-271, XP002583037 ISSN: 0075-4617.
Aden, A, et al, "Top Value Added Chemicals From Biomass," U.S. Department of Energy, Aug. 2004, 76 pages.
Corma, A. et al., "Chemical Routes for the Transformation of Biomass into Chemicals," Chem. Rev., 2007, vol. 107, pp. 2411-2502.
Ferguson, L.N. et al., "Selective Oxidation of Alkyl Groups," Journal of Organic Chemistry, Apr. 1960, vol. 25, pp. 668-670.
Monteiro, J.L.F. et al., "Catalytic conversion of terpenes into fine chemicals," Topics in Catalysis, Feb. 2004, vol. 27, Nos. 1-4, pp. 169-180.
Okkerse, C. et al. "From fossil to green," Green Chemistry, Apr. 1999, pp. 107-114.
Ravasio, N. et al., "Mono- and bifunctional hetrogeneous catalytic transformation of terpenes and terpenoids," Topics in Catalysis, Feb. 2004, vol. 27, Nos. 1-4, pp. 157-168.
Swift, K.A.D., "Catalytic transformations of the major terpene feedstocks," Topics in Catalysis, Feb. 2004, vol. 27, Nos. 1-4, pp. 143-155.
Tavener, S. et al., "Teaching green chemistry: from lemons to lemonade bottles," Green Chemistry, Jun. 2003, G46-G48.
Varadarajan, S. et al., "Catalytic Upgrading of Fermentation-Derived Organic Acids," Biotechnol. Prog. 1999, vol. 15, pp. 845-854.

(Continued)

*Primary Examiner* — Yevegeny Valenrod
(74) *Attorney, Agent, or Firm* — Cantor Colburn LLP

(57) ABSTRACT

Bio-based terephthalic acid (bio-TPA), bio-based dimethyl terephthalate (bio-DMT), and bio-based polyesters, which are produced from a biomass containing a terpene or terpenoid, such as limonene are described, as well as the process of making these products. The bio-based polyesters include poly (alkylene terephthalate)s such as bio-based poly(ethylene terephthalate) (bio-PET), bio-based poly(trimethylene terephthalate) (bio-PTT), bio-based poly(butylene terephthalate) (bio-PBT), and bio-based poly(cyclohexylene dimethyl terephthalate) (bio-PCT).

12 Claims, No Drawings

(56) References Cited

OTHER PUBLICATIONS

Khan et al; "cotonoates A and B, New Aromatic Ester from *Cotoneaster racemifloras*"; Zeitschrift fur Naturforschung B (Chemical Sciences); 2008; 63b; pp. 1219-1222.
Rieckmann et al.; Modern Polyesters; Chapter II; "Poly(ethylene terephthalate) Polymerization"; Article and Abstract; Published Online; Jun. 21, 2004.
Talapatra et al.; "Polyphenalic Constituents of *Magnolia pterocarpa* Roxb."; Journal of the Indian Chemical Society; 1983; 60; pp. 96-98.
Talapatra et al.; "On the Chemistry of Indian Orchidaceae Plants—II"; Tetrahedron; 1985; 41; pp. 2765-2769.
Thakur et al.; Terephthalic Acid and its Methyl Esters: from *Zizyphus sativa*; Planta Medica; 1975; 28; pp. 172-173; Abstract.
CN101045938 A; Abstract; Oct. 3, 2007; 1 page.
IN195695; Abstract; Jul. 31, 2009; 2 pages.
JP2006328375 A; Abstract; Dec. 7, 2006; 1 page.
JP2006328378 A; Abstract; Dec. 7, 2006; 1 page.
JP2008094888 A; Abstract; Apr. 24, 2008; 1 page.
JP2009013094 A; Abstract; Jan. 22, 2009; 1 page.
WO2009014225 A1; Abstract; Jan. 29, 2009; 1 page.
WO2009072462 A1; Abstract; Jun. 11, 2009; 1 page.
JP2009209145 A; Abstract; Sep. 17, 2009; 1 page.
IN214058; Abstract; Mar. 28, 2008; 2 pages.
Akiyoshi; "Study Concerning Terylene (2nd Report) Terephthalic acid synthesis via p-cymene"; English Translation with Letter of Certification; Department of Applied Chemistry; Date of Acceptance Jul. 4, 1951; 4 pages.
Borgwardt; "Methanol Production from Biomass and Natural Gas as Transportation Fuel"; Ind. Eng. Chem. Res.; 1998; 37; pp. 3760-3767.
Buhl et al.; "Preparation of p-Cymene from Mixtures of Terpenes as Renewable Feedstock"; Science and Technoloby in Catalysis; 1998; vol. 24; pp. 191-196.
Buhl et al., "Production of p-cymene from a-limonene over silica supported Pd catalysts", Applied Catalysis A: General 188, 1999, pp. 287-299.
Carlson et al., "Green Gasoline by Catalytic Fast Pyrosis of Solid Biomass Derived Compounds", Chem. Sus. Chem. 1, 2008, pp. 397-400.
Hosokai et al., "Activity of Mesoporous Alumina Particles for Biomass Steam Reforming in a Fluidized-Bed Reactor and Its Application to a Dual-Gas-Flow Two-Stage Reactor System", Ind. Eng. Chem. Res. 47, 2008, pp. 5346-5352.
Katikeneni et al.; "Potential of Producing High Octane Additives and Hydrogen from Biomass-Derived Oils"; Proceedings of the Intersociety Energy Conversion Engineering Conference; 1997; 32nd; pp. 1773-1778.
Kaufmann et al.; Diels-Alder reactions in the field of fats VIII, The reaction of polyunsaturated fatty acids and drying oils with acetylene; a new synthesis of terephthalic acid:; The Institute for Industrial Research, Munster (Westf.); Fette-Seifen-Anstrichmittel; 65; No. 10; 1963; 9 pages; English Translation with Certificate.
Kaufmann et al.; Diene syntheses in the field of fats. Part VII: The reaction of drying oils with ethylene and its homologs:; The German Institute for Fats Reaearch, Munster (Westf.); Fette-Seifen-Anstrichmittel; 65; No. 2, 1963; 14 pages; English Translation with Certificate.
Limonene Practical, last downloaded from http://www.greenchemistrynetwork.org/pdf/LimonenePractical.pdf on Dec. 21, 2011, 14 pages.
Liu et al.; "Preparation of biopolymers from liguefied corn stover"; Transactions of the Chinese Society of Agricultural Engineering; 21(12); 2005; pp. 116-120.
Martin-Luengo et al., "Synthesis of p-cymene from limonene, a renewable feedstock", Applied Catalysis B: Environmental 81, 2008, pp. 218-224.
Odling; Proceedings of Societies—Chemical Society, Ordinary Meeting; "Action of Acid Chlorides on Nitrates and Nitrites"; The Chemical News and Journal of Physical Science; vol. 27-2/8; p. 179-180; Apr. 10, 1873.
Palani et al.; "Esterification of terephthalic acid with methanol over mesoporous A1-MCM-41 molecular sieves"; Journal of Molecular Catalysis A: Chemical 245; 2006; pp. 101-105.
International Preliminary Report on Patentability for International Application No. PCT/US2009/069691; International Filing Date Dec. 29, 2009; Date of Issuance Jul. 5, 2011; 11 pages.
International Search Report for International Application No. PCT/US2009/069691; International Filing Date Dec. 29, 2009; Date of Mailing Sep. 17, 2010; 6 pages.
Written Opinion for International Application No. PCT/US2009/069691; International Filing Date Dec. 29, 2009; Date of Mailing Sep. 17, 2010; 10 pages.
Raja et al., "Shape-Selective Regiospecific and bifunctional Nanoporous Catalysts for Single Step Solvent Free Processes", Nanotechnology in Catalysis, 2004, pp. 249-272.
Roberge et al., "Catalytic aspects in the transformation of pinenes to p-cymene", Applied Catalysis A: General 215, 2001, pp. 111-124.
Schwanert H.; English Translation with Certification of "Ueber Terephtalsaure und Camphresinsaure"; Liebigs Annalen Der Chemie Unk Pharmacie; vol. 132; No. 3; 1864; XP002583037; ISSN: 0075-4617; 29 pages.
Senseman et al., "Catalytic Oxidation of p-Cymene in the Vapor Phase", Industrial and Engineering Chemistry, vol. 23, No. 10, 1931, pp. 1129-1131.
Sugimori et al., "Microbial Hydroxylation of Indole to 7-Hydroxyindole by *Acinetobacter calcoaceticus* Strain 4-1-5", Biosci. Biotechnol. Biochem. 68 (5), 2004, pp. 1167-1169.
Wang et al.; "A Method for Producing Terephthalic Acid by Comamonas testosterone DSM6577"; Cuihua Xuebao; vol. 27; No. 4; pp. 297-298; 2006.
Wang et al.; "Conversion of Plant-Biomass to BTX and Synthetic Fuels by Catalytic Pyrolysis" with English Abstract; Huagong Xuebou (Chinese Edition); 2004; 55(8); 1341-1347.
Wang et al.; "Biotransformation of p-toluic acid into terephthalic acid by Comamonas testosterone DSM6577" with English Abstract; Chinese Journal of Bioprocess Engineering; 3(4); 2005; pp. 19-22.
Wang et al.; "Effect of operation conditions on light aromatic hydrocarbon yield of catalytic pyrolysis of biomass"; Chinese Journal of Bioprocess Engineering 54; Nov. 2007; Abstract; 6 pages.
Wang et al.; "Production of Light Aromatic Hydrocarbons from Biomass by Catalytic Pyrolysis"; Science Diet; Chinese Journal of Catalysis; vol. 29; Issue 9; Sep. 2008; pp. 907-912.
You; "Recent Trends of Biosynthesis to Replacement of Petroleum by Carbohydrate" with English Abstract; Fine and Specialty Chemicals; vol. 1 15; No. 5; pp. 25-28; Jan. 10, 2007.
Yu et al. "Liquefaction of Corn Stover and Preparation of Polyester from the Liquified Product"; Applied Biochemistry and Biotechnology; 2006; vol. 129-132; pp. 574-585.
Pinkowska; "Green Methods Used to Produce Intermediates for Synthesis of Polymers"; University of Economics, Wroclaw; 2006; with Letter of Certification; 16 pages.
Ribiero et al.; "Synthesis of 2,5-Furandicarboxylic Acid from Fructose: A Suitable Precursor for Biopolymers"; Natural Polymers and Composites IV; Proceedings from the International Symposium on Natural Polymers and Composites; Sao Pedro, Brazil; Sep. 1-4, 2002; pp. 192-197.
Wrobel; "The Use of Muconic Acid Ethyl Ester for Diels-Adler Reaction"; Dept. of Organic Chemistry; 1951; with Letter of Certification; 4 pages.

* cited by examiner

BIO-BASED TEREPHTHALATE POLYESTERS

Several scientific studies strongly suggest that petroleum feed stocks will be exhausted around year 2050 if the present consumption of fossil stocks will continue at a constant rate. See, for example, US Department of Energy: Top value Added Chemicals from biomass. Vol 1. August 2004; Okkerse, C. et al., *Green Chemistry* (1999), 1(2), 107-114; and Corma, A., et al., *Chemical Reviews* (2007), 107(6), 2411-2502.

The Kyoto protocol together with the desire to reduce society's dependence on imported crude oil has directed researcher's attention toward the use of biomass as source of energy and of commodity chemicals. Further, the cost of petroleum feed stocks has risen dramatically and there is a rising consumer interest in using "green", or renewable resources as the basis for consumer products.

Therefore, the era of a chemical industry based on fossil resources will probably come to an end before the end of the century.

Terephthalic acid, is a commodity chemical, principally used as a starting compound for the manufacture of various polyesters, specifically poly(ethylene terephthalate) (PET), which is used in clothing and to make plastic bottles. Terephthalic acid is produced on an industrial scale by oxidation of para-xylene by oxygen from air in the presence of a catalyst. However, this synthetic route to terephthalic acid and poly (terephthalates) will either become prohibitively expensive, as the cost of petroleum rises, or unavailable as petroleum resources become scarce.

Nature produces a vast amount of biomass per year by photosynthesis. See, e.g., Corma, A., et al., *Chemical Reviews* (2007), 107(6), 2411-2502. Terpenes are a large and varied class of naturally occurring hydrocarbons that are formed by units of isoprene ordered in a regular pattern. Terpenes and other terpenoids are produced primarily by a wide variety of plants and are a natural and sustainable supply of chemical building blocks. For example, world production of turpentine oil in 1995 was 330000 tons while limonene production was around 30000 tons per year. See, e.g., Swift K. A. D., *Topics in Catalysis* (2004), 27(1-4), 143-155.

As described above, terpenes are available as potential candidates for natural feedstock, or bio-based chemicals. However, the use of terpenes as a natural feedstock to prepare aromatic groups, such as terephthalic acid (TPA), to be used for the preparation of thermoplastic polyesters is not currently known.

Therefore, there is a need for bio-based polyesters, produced from a biomass source. There is also a need for bio-based terephthalic acid and bio-based dimethyl terephthalate, produced from a biomass source, to produce the bio-based polyesters, such as PET and other poly(terephthalates).

SUMMARY

Bio-based terephthalic acid, bio-based dimethyl terephthalate, and bio-based polyesters are described herein. The compounds and processes described herein satisfy the above-described need for bio-based polyesters, bio-based terephthalic acid, and bio-based dimethyl terephthalate, which are produced from a biomass source.

According to one embodiment, a bio-based terephthalic acid of Formula I is provided.

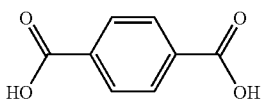

Formula I

Wherein the bio-based terephthalic acid has a mean bio-based content of at least 5%. Preferably, the bio-based terephthalic acid has a mean bio-based content of at least 80%, and more preferably, of at least 90%.

According to one embodiment, the bio-based terephthalic acid of Formula I is prepared from a biomass. According to the process, first a "biomass", which is a biological material excluding organic material that has been transformed by geological processes into a member selected from the group consisting of petroleum, petrochemicals, and combinations thereof is provided. The biomass is then converted to terephthalic acid, preferably substantially in the absence of chromium oxide.

Preferably, the process of making the bio-based terephthalic acid of Formula I comprises providing a biomass comprising a terpene, terpenoid or a mixture thereof, and converting the terpene, terpenoid, or mixture thereof to para-cymene. The para-cymene is then converted to terephthalic acid by oxidation, the oxidation being performed substantially in the absence of chromium oxide.

The oxidation step is preferably a two-step oxidation, and more preferably, a two step oxidation comprising a first step using a mineral acid, and a second step using a transition metal oxidant, such as a permanganate compound. Also preferably, the process is performed substantially in the absence of chromium, and the oxidation step has a total yield of at least 85%.

Preferably, the terpene or terpenoid has a mono-cyclic or bi-cyclic structure, and/or the terpene or terpenoid has ten carbon atoms in the chemical formula. The terpene or terpenoid may be selected from the group consisting of borneol, camphene, camphor, careen, camphene, carvacrol, carvone, cineole, eucalyptol, limonene, phellandrene, dipentene, pinene, sabinene, terpineol, terpinene, terpinolene, thujene, thymol, and combinations thereof. More preferably, the terpene is limonene.

The terpene, terpenoid, or mixture thereof may be converted to para-cymene in the presence of a catalyst selected from the group consisting of metal catalysts, amine catalysts, and combinations thereof. Also, the terpene, terpenoid, or mixture thereof may be converted to para-cymene in the presence of a catalyst selected from the group consisting of transition metal catalysts, Group IA catalysts, amine catalysts, and combinations thereof. Preferably, the para-cymene is produced at a yield of at least 70% from the terpene, terpenoid, or combination thereof, more preferably, at a yield of at least 95% from the terpene, terpenoid, or combination thereof.

According to another embodiment of the invention, a compound comprising bio-based dimethyl terephthalate of Formula II is provided.

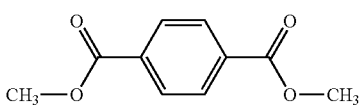

Formula II

The bio-based dimethyl terephthalate has a mean bio-based content of at least 5%. Preferably, the bio-based dimethyl terephthalate has a mean bio-based content at least 80%, and more preferably, at least 90%.

The bio-based dimethyl terephthalate may be made by a process comprising converting bio-based terephthalic acid to bio-based dimethyl terephthalate by esterification of the bio-based terephthalic acid. Alternately, the bio-based dimethyl terephthalate of Formula II may be prepared by a process comprising first providing a biomass as described above, and then converting the biomass to bio-based terephthalic acid of Formula I.

Preferably, the process of making bio-based dimethyl terephthalate of Formula II comprises first providing a biomass comprising a terpene, terpenoid or a mixture thereof, and then converting the terpene, terpenoid, or mixture thereof to bio-based para-cymene. The bio-based para-cymene is then converted to bio-based terephthalic acid of Formula I by an oxidation performed substantially in the absence of chromium oxide, and then the bio-based terephthalic acid with methanol selected from the group consisting of bio-based methanol, petroleum based methanol, and combinations thereof to provide the bio-based dimethyl terephthalate of Formula II. More preferably, the bio-based terephthalic acid of Formula I is converted to bio-based dimethyl terephthalate of Formula II with bio-based methanol, the bio-based methanol having a mean bio-based content of at least 90%.

According to another embodiment, the process further comprises mixing the bio-based terephthalic acid of Formula I with petroleum based terephthalic acid to make a mixture of bio-based terephthalic acid and petroleum based terephthalic acid.

According to another embodiment of the invention, a polymer compound comprising bio-based poly(alkylene terephthalate) of Formula III is provided.

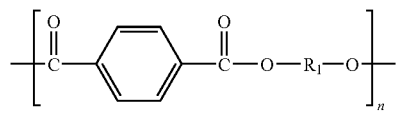

Formula III

Wherein $R_1$ is selected from the group consisting of alkyl, cycloalkyl, cycloalkylene alkyl, and cycloalkylene dialkyl groups having from two to ten carbons, and n is an integer between about 50 and about 130.

The bio-based poly(alkylene terephthalate) of Formula III has a mean bio-based content of at least 5%. Preferably, the bio-based poly(alkylene terephthalate) of Formula III has a mean bio-based content of at least 60%, more preferably, at least 80%, and most preferably, at least 90%.

According to one embodiment of the invention, in the compound of Formula III, $R_1$ is a bio-based group selected from the group consisting of bio-based alkyl, bio-based cycloalkyl, bio-based cycloalkylene alkyl, and bio-based cycloalkylene dialkyl groups having from two to ten carbons. According to another embodiment, $R_1$ is an alkyl group of the formula $-(CH_2)_m-$, wherein m is an integer from two to four, and preferably, $R_1$ is a bio-based alkyl group of the formula $-(CH_2)_m-$, wherein m is an integer from two to four. According to another embodiment $R_1$ may also be a cycloalkylene dialkyl group, preferably, according to this embodiment, $R_1$ is a bio-based cycloalkylene dialkyl group.

According to another embodiment of the invention, a process for preparing a bio-based poly(alkylene terephthalate) of Formula III is provided. According to the process, first, a biomass, as described above, is provided. The biomass is then converted to bio-based terephthalic acid, and the bio-based terephthalic acid is then converted to the bio-based poly(alkylene terephthalate) of Formula III.

According to another embodiment, the process of converting the bio-based terepththalic acid is performed by first converting the bio-based terephthalic acid to bio-based dimethyl terephthalate.

According to another embodiment, the bio-based dimethyl terepththalate and/or terephthalic acid is converted to the bio-based poly(alkylene terephthalate) of Formula III by reacting the bio-based dimethyl terephthalate and/or terephthalic acid with a diol of the formula:

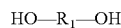

Where $R_1$ is an alkyl group of the formula $-(CH_2)_m-$, wherein m is an integer from two to four. Preferably, the diol is at least in part a bio-based diol, the diol having a mean bio-based content of at least 80%.

According to another embodiment of the invention, a polymer compound comprising bio-based poly(butylene terephthalate) of Formula IV is provided.

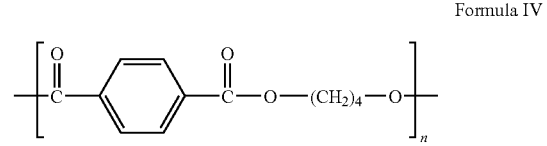

Formula IV

Wherein n is an integer of between about 50 and about 130.

The bio-based poly(butylene terephthalate) of Formula IV has a mean bio-based content of at least 5%. Preferably, the bio-based poly(butylene terephthalate) has a mean bio-based content of at least 50%, more preferably, at least 80%, and most preferably, at least 90%. the bio-based poly(butylene terephthalate) is made by a process comprising reacting bio-based dimethyl terephthalate with 1,4-butane diol.

According to another embodiment of the invention, the bio-based poly(butylene terephthalate) of Formula IV may be prepared by reacting the bio-based dimethyl terephthalate of Formula II and/or terephthalic acid of Formula I with 1,4-butane diol. In a preferred embodiment, the bio-based poly(butylene terephthalate) of Formula IV is made by a process comprising reacting bio-based dimethyl terephthalate with 1,4-butane diol selected from the group consisting of petroleum based 1,4-butane diol, bio-based 1,4-butane diol, and combinations thereof. More preferably, the bio-based poly(butylene terephthalate) is made by a process comprising reacting bio-based dimethyl terephthalate with a 1,4-butane diol that is at least in part bio-based 1,4-butane diol.

According to another embodiment of the invention, a polymer compound comprising bio-based poly(trimethylene terephthalate) of Formula V is provided.

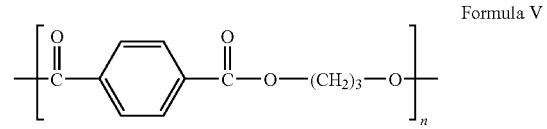

Formula V

Wherein n is an integer of between about 50 and 130.

The bio-based poly(trimethylene terephthalate) of Formula IV has a mean bio-based content of at least 5%. Preferably, the bio-based poly(trimethylene terephthalate) has a mean bio-based content of at least 33%, more preferably, of at least 80%, and most preferably, of at least 90%.

According to another embodiment of the invention, the bio-based poly(trimethylene terephthalate) of Formula IV may be prepared by reacting the bio-based dimethyl terephthalate of Formula II and/or terephthalic acid of Formula I with 1,3-propane diol. In a preferred embodiment, the bio-based poly(trimethylene terephthalate) is made by a process comprising reacting bio-based dimethyl terephthalate with 1,3-propane diol selected from the group consisting of petroleum based 1,3-propane diol, bio-based 1,3-propane diol, and combinations thereof. More preferably, the 1,3-propane diol is at least in part bio-based 1,3-propane diol, and most preferably, the 1,3-propane diol is at least in part bio-based 1,3-propane diol, the 1,3-propane diol having a mean bio-based content of at least 80%.

According to another embodiment of the invention, a polymer compound comprising bio-based poly(ethylene terephthalate) of Formula VI is provided.

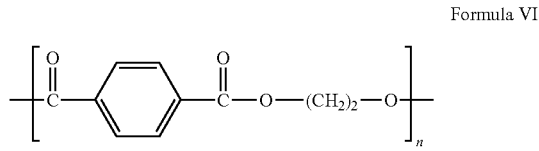

Formula VI

Wherein n is an integer of between about 50 and about 130; and

The bio-based poly(ethylene terephthalate) of Formula VI has a mean bio-based content of at least 5%. Preferably, the bio-based poly(ethylene terephthalate) has a mean bio-based content of at least 33%, more preferably, at least 80%, and most preferably, at least 90%.

According to another embodiment of the invention, the bio-based poly(ethylene terephthalate) of Formula VI may be prepared by reacting the bio-based dimethyl terephthalate of Formula II and/or terephthalic acid of Formula I with ethylene glycol. In a preferred embodiment, the bio-based poly(ethylene terephthalate) is made by a process comprising reacting bio-based dimethyl terephthalate with ethylene glycol selected from the group consisting of petroleum based ethylene glycol, bio-based ethylene glycol, and combinations thereof. Preferably, the bio-based poly(ethylene terephthalate) is made by a process comprising reacting bio-based dimethyl terephthalate with ethylene glycol that is at least in part bio-based ethylene glycol, and more preferably, the ethylene glycol is at least in part bio-based ethylene glycol, having a mean bio-based content of at least 80%.

According to another embodiment of the invention, a compound comprising bio-based 1,4-cyclohexane dimethanol of Formula VII is provided.

Formula VII

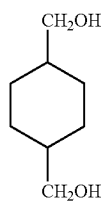

The bio-based 1,4-cyclohexane dimethanol has a mean bio-based content of at least 5%. Preferably, the bio-based 1,4-cyclohexane dimethanol has a mean bio-based content of at least 80%, and more preferably, at least 90%.

According to another embodiment of the invention, a process of making a compound comprising bio-based 1,4-cyclohexane dimethanol of Formula VII is provided. According to the process, first, a biomass, as described above, comprising a terpene, terpenoid or a mixture thereof is provided. Then, the terpene, terpenoid, or mixture thereof is converted to para-cymene, and the para-cymene is converted to terephthalic acid by oxidation, the oxidation being performed in the absence of chromium oxide. The terephthalic acid is then converted to the bio-based 1,4-cyclohexane dimethanol of Formula VII.

According to another embodiment of the invention, a polymer compound comprising bio-based poly(cyclohexylene dimethylene terephthalate) of Formula VIII is provided.

Formula VIII

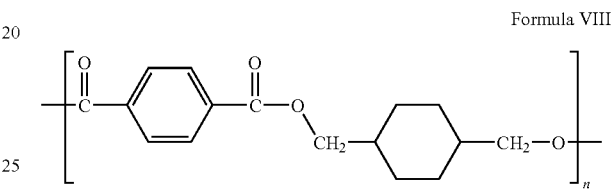

Wherein n is an integer between about 50 and about 130.

The bio-based poly(cyclohexylene dimethylene terephthalate) has a mean bio-based content of at least 5%. Preferably, the bio-based poly(cyclohexylene dimethylene terephthalate) has a mean bio-based content of at least 80%, and more preferably, at least 90%.

According to another embodiment of the invention, the bio-based poly(cyclohexylene dimethylene terephthalate) of Formula VIII may be prepared by reacting the bio-based dimethyl terephthalate of Formula II and/or terephthalic acid of Formula I with 1,4-cyclohexane. In a preferred embodiment, the bio-based poly(cyclohexylene dimethylene terephthalate) is made by a process comprising reacting bio-based dimethyl terephthalate with a 1,4-cyclohexane dimethanol selected from the group consisting of petroleum based 1,4-cyclohexane dimethanol, bio-based 1,4-cyclohexane dimethanol, and combinations thereof. Also preferably, the bio-based dimethyl terephthalate has a mean bio-based content of at least 5%, and/or the bio-based 1,4-cyclohexane dimethanol has a mean bio-based content of at least 5%. More preferably, the bio-based dimethyl terephthalate has a mean bio-based content of at least 80%, and/or the bio-based 1,4-cyclohexane dimethanol has a mean bio-based content of at least 80%, and most preferably, the bio-based dimethyl terephthalate has a mean bio-based content of at least 90%, and/or the bio-based 1,4-cyclohexane dimethanol has a mean bio-based content of at least 90%.

DESCRIPTION

According to one embodiment of the present invention, a biomass, such as terpenes and terpenoids, and mixtures thereof, is converted to bio-based terephthalic acid (TPA) and bio-based di-methyl terephthalate (DMT). In particular, both α- and β-pinene, the main component of turpentine oil, and limonene, the main component of lemon essential oil, posses a six member hydrocarbon ring. As described herein, these terpenes are an available biomass source, and may be transformed into six member ring aromatic compounds such as para-cymene, which is then converted to bio-based terephthalic acid (bio-TPA) and bio-based di-methyl terephthalate (bio-DMT). The bio-TPA and bio-DMT may be subsequently polymerized to form bio-based polyesters, such as bio-based poly(ethylene terephthalate) (bio-PET), bio-based poly(trimethylene terephthalate) (bio-PTT), and bio-based poly(butylene terephthalate) (bio-PBT). A biomass is also converted to bio-based cyclohexane di-methanol and polymerized with bio-based terephthalic acid or bio-based di-methyl terephthalate (bio-DMT) to produce bio-based poly(cyclohexylene dimethyl terephthalate) (bio-PCT).

As used in this disclosure, the following terms have the following meanings:

The term "bio-based" means a compound, composition and/or other organic material that is "isotopically rich" in carbon 14 as compared to a petroleum source, as determined by ASTM D6866.

The term "bio-mass" means living and recently dead biological material which excludes organic material that has been transformed by geological processes into a member selected from the group consisting of petroleum, petrochemicals, and combinations thereof.

The term "isotopically rich" means a higher carbon 14 to carbon 12 ratio in a compound, composition and/or other organic material as compared to the carbon 14 to carbon 12 ratio in a petroleum source.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed in this patent application. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The term "from more than 0 to" an amount means that the named component is present in some amount more than 0, and up to and including the higher named amount.

According to one embodiment of the present invention, there is provided bio-based terephthalic acid of Formula I:

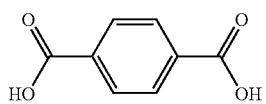

Formula I

According to this embodiment of the invention, at least 5% of the terephthalic acid of formula I is bio-based terephthalic acid. In a preferred embodiment, at least 80% of the terephthalic acid of formula I is bio-based terephthalic acid, and more preferably, at least 90% of the terephthalic acid of formula I is bio-based terephthalic acid.

The bio-based terephthalic acid of formula I is prepared from a biomass which is converted, substantially in the absence of chromium oxide to the bio-based terephthalic acid of Formula I.

According to another embodiment of the invention, a bio-based dimethyl terephthalate of Formula II is provided:

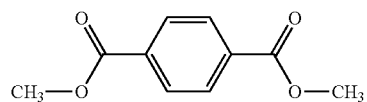

Formula II

According to this embodiment of the invention at least 5% of the dimethyl terephthalate is bio-based dimethyl terephthalate, and more preferably, at least 80% of the dimethyl terephthalate is bio-based dimethyl terephthalate, and most preferably, at least 90% of the dimethyl terephthalate is bio-based dimethyl terephthalate.

The bio-based dimethyl terephthalate of Formula II is prepared by converting the bio-based terephthalic acid to bio-based dimethyl terephthalate of Formula II with methanol. The methanol may be bio-based methanol, petroleum based methanol, and/or a combinations thereof.

The bio-based terephthalic acid (bio-TPA) of Formula I and the bio-based dimethyl terephthalate (bio-DMT) of Formula II may be converted to various bio-based polyesters, such as poly(ethylene terephthalate) (bio-PET), poly(trimethylene terephthalate) (bio-PTT), and poly(butylene terephthalate) (bio-PBT). A biomass, as described herein, may also be converted to bio-based cyclohexane di-methanol and converted with bio-based terephthalic acid (bio-TPA) or bio-based di-methyl terephthalate (bio-DMT) to produce bio-based poly(cyclohexylene dimethyl terephthalate) (bio-PCT). However, other polymers may be produced with the compounds and methods described herein, as will be understood by those of skill in the art by reference to this disclosure.

According to another embodiment of the invention a polymer compound comprising bio-based poly(alkylene terephthalate) of Formula III is provided.

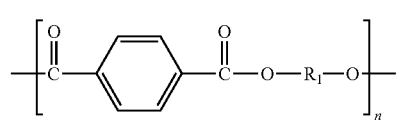

Formula III wherein
$R_1$ is selected from the group consisting of alkyl, cycloalkyl, cycloalkylene alkyl, and cycloalkylene dialkyl groups having from two to ten carbons,
n is an integer between about 50 and about 130; and
In the bio-based poly(alkylene terephthalate) represented by Formula III above, at least 5% of the poly(alkylene terephthalate) is bio-based poly(alkylene terephthalate). Preferably, at least 60% of the poly(alkylene terephthalate) is bio-based poly(alkylene terephthalate), and more preferably, at least 80% of the poly(alkylene terephthalate) is bio-based poly(alkylene terephthalate), and most preferably, at least 90% of the poly(alkylene terephthalate) is bio-based poly(alkylene terephthalate).

In the bio-based poly(alkylene terephthalate) represented by Formula III, $R_1$ is petroleum based, bio-based, or a combination thereof. In a preferred embodiment, $R_1$ is a bio-based group selected from the group consisting of bio-based alkyl, bio-based cycloalkyl, bio-based cycloalkylene alkyl, and bio-based cycloalkylene dialkyl groups having from two to ten carbons, and $R_1$ is a bio-based or petroleum based alkyl group of the formula —$(CH_2)_m$—, wherein m is an integer from two to four, or $R_1$ is a bio-based or petroleum based cycloalkylene dialkyl group. More preferably, $R_1$ is a bio-based alkyl group of the formula —$(CH_2)_m$—, wherein m is an integer from two to four, such as bio-based ethyl, propyl, and butyl substituents, or $R_1$ is a bio-based cycloalkylene dialkyl group, such as bio-based cyclohexylene dimethyl.

According to another embodiment of the invention a polymer compound comprising bio-based poly(butylene terephthalate) of Formula IV is provided.

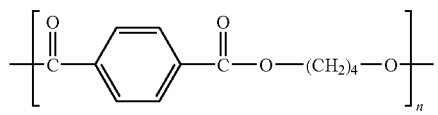

Formula IV wherein n is an integer of between about 50 and about 130.

In the bio-based poly(butylene terephthalate) of Formula IV above, at least 5% of the poly(butylene terephthalate) is bio-based poly(butylene terephthalate). Preferably, at least 50% of the poly(butylene terephthalate) is bio-based poly(butylene terephthalate). More preferably, at least 80% of the poly(butylene terephthalate) is bio-based poly(butylene terephthalate), and most preferably, at least 90% of the poly(butylene terephthalate) is bio-based poly(butylene terephthalate).

The butylene group, $(CH_2)_4$, as shown in the Formula IV above may be petroleum based, bio-based, or a combinations thereof, with bio-based butylene, $(CH_2)_4$, being preferred.

According to another embodiment of the invention, a polymer compound comprising bio-based poly(trimethylene terephthalate) of Formula V is provided.

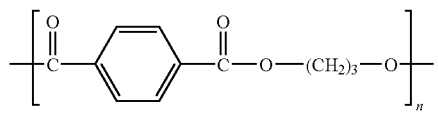

Formula V wherein n is an integer of between about 50 and 130.

In the bio-based poly(trimethylene terephthalate) of Formula V, at least 5% of the poly(trimethylene terephthalate) is bio-based poly(trimethylene terephthalate). Preferably, at least 33% of the poly(trimethylene terephthalate) is bio-based poly(trimethylene terephthalate). More preferably, at least 80% of the poly(trimethylene terephthalate) is bio-based poly(trimethylene terephthalate), and most preferably, at least 90% of the poly(trimethylene terephthalate) is bio-based poly(trimethylene terephthalate).

The trimethylene group, —$(CH_2)_3$—, as shown in the Formula V above may be petroleum based, bio-based, or a combinations thereof, with bio-based trimethylene, —$(CH_2)_3$—, being preferred.

According to another embodiment of the invention a polymer compound comprising bio-based poly(ethylene terephthalate) of Formula VI is provided.

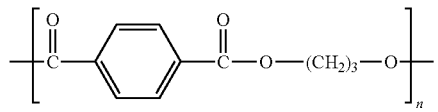

VI wherein n is an integer of between about 50 and about 130.

In the bio-based poly(ethylene terephthalate) of Formula VI, at least 5% of the poly(ethylene terephthalate) is bio-based poly(ethylene terephthalate). Preferably, at least 33% of the poly(ethylene terephthalate) is bio-based poly(ethylene terephthalate). More preferably, at least 80% of the poly(ethylene terephthalate) is bio-based poly(ethylene terephthalate), and most preferably, at least 90% of the poly(ethylene terephthalate) is bio-based poly(ethylene terephthalate).

The ethylene group, —$(CH_2)_2$—, as shown in the Formula VI above may be petroleum based, bio-based, or a combinations thereof, with bio-based ethylene, —$(CH_2)_2$—, being preferred.

According to another embodiment of the invention, a compound comprising bio-based 1,4-cyclohexane dimethanol of Formula VII is also provided.

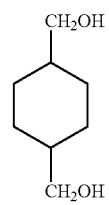

Formula VII

The bio-based 1,4-cyclohexane dimethanol of Formula VII above, is prepared from a biomass and at least 5% of the 1,4-cyclohexane dimethanol is bio-based 1,4-cyclohexane dimethanol. Preferably, at least 80% of the 1,4-cyclohexane dimethanol is bio-based 1,4-cyclohexane dimethanol, and more preferably, at least 90% of the 1,4-cyclohexane dimethanol is bio-based 1,4-cyclohexane dimethanol.

According to another embodiment of the invention, a polymer compound comprising bio-based poly(cyclohexylene dimethyl terephthalate) of Formula VIII is provided.

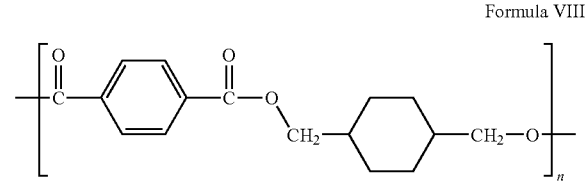

Formula VIII wherein n is an integer between about 50 and about 130; and

In the bio-based poly(cyclohexylene dimethyl terephthalate) shown in Formula VIII above, at least 5% of the poly(cyclohexylene dimethyl terephthalate) is bio-based poly(cyclohexylene dimethyl terephthalate). Preferably, at least 80% of the poly(cyclohexylene dimethyl terephthalate) is bio-based poly(cyclohexylene dimethyl terephthalate), and more preferably, at least 90% of the poly(cyclohexylene dimethyl terephthalate) is bio-based poly(cyclohexylene dimethyl terephthalate).

The bio-based poly(cyclohexylene dimethyl terephthalate) (bio-PCT) of Formula VIII may be prepared by converting bio-based 1,4-cyclohexane dimethanol of Formula VII, or petroleum based 1,4-cyclohexane dimethanol, and/or a combination thereof with bio-based terephthalic acid (bio-TPA), or bio-based dimethyl terephthlate (bio-DMT) to produce the bio-PCT, preferably, bio-based 1,4-cyclohexane dimethanol is converted with bio-TPA and/or bio-DMT to produce the bio-PCT.

According to the invention, the bio-based terephthalic acid (bio-TPA) and bio-based dimethyl terephthlate (bio-DMT) may be used to produce other bio-based polymers, such as bio-based PCTG, elastomeric polyesters, liquid crystalline polyarylates and their blends with traditional thermoplastic polymers.

According to another embodiment of the invention, a process for preparing bio-terephthalic acid (bio-TPA) and bio-dimethyl terephthalate (bio-DMT) is provided. An example of the process of the invention is represented in Scheme I below.

Scheme I

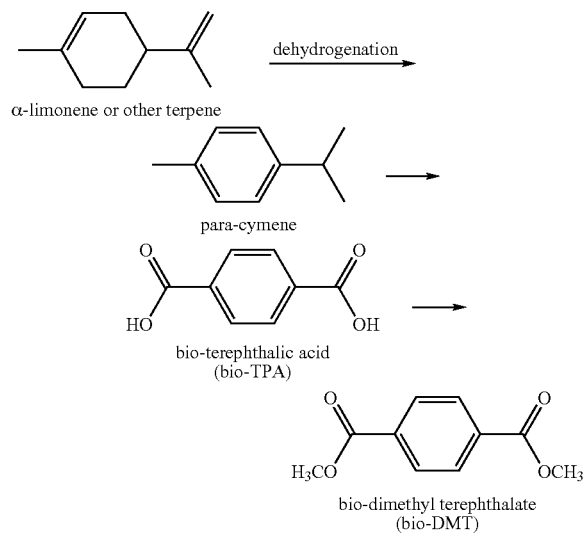

As shown in Scheme I, a biomass, containing a terpene, terpenoid, or combination thereof, such as limonene, is converted in three steps to bio-terephthalic acid. The bio-terephthalic acid is then converted with methanol to bio-dimethyl terephthalate. In this manner, bio-TPA and bio-DMT, two building blocks for bio-polymers are produced in high yield.

Step one of the process of the invention is shown in Scheme II below.

Scheme II

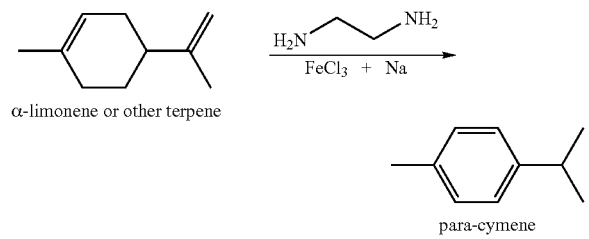

As shown in Scheme II, a terpene, such as α-limonene, obtained from a biological source, such as from lemons. The terpene may be selected from the group consisting of borneol, camphene, camphor, careen, camphene, carvacrol, carvone, cineole, eucalyptol, limonene, phellandrene, dipentene, pinene, sabinene, terpineol, terpinene, terpinolene, thujene, thymol, and combinations thereof. Preferably, the terpene or terpenoid has a mono-cyclic or bi-cyclic structure, and/or the terpene or terpenoid has ten carbon atoms in the chemical formula. More preferably, the terpene is limonene.

The terpene, obtained from a biomass, is dehydrogenated with a catalyst, such as ethylenediamine and anhydrous FeCl$_3$ to produce bio-based para-cymene. Preferably, the dehydrogenation catalyst is a catalyst selected from the group consisting of metal catalysts, amine catalysts, and combinations thereof. Preferably, the para-cymene is produced at a yield of at least 70% from the terpene, terpenoid, or combination thereof, and more preferably, the para-cymene is produced at a yield of at least 95% from the terpene, terpenoid, or combination thereof.

Steps two and three of the process of the invention are shown in Scheme III below.

Scheme III.

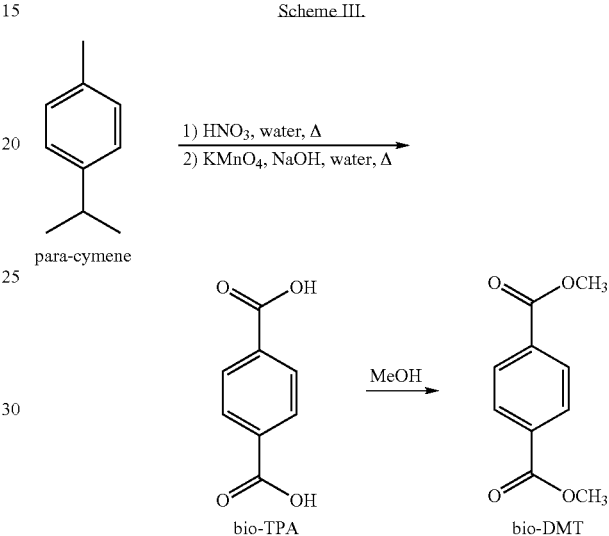

In step two of the process, para-cymene is converted to bio-TPA in the presence of an oxidation catalyst, such as potassium permanganate. The para-cymene is converted to bio-based terephthalic acid substantially in the absence of chromium oxide, and more preferably substantially in the absence of chromium. Also preferably, The para-cymene is converted to bio-based terephthalic acid in a two-step oxidation comprising i) a first step using a mineral acid, and ii) a second step using a transition metal oxidant. The two-step oxidation has been found to have a total yield of at least 85%.

The terephthalic acid produced by the above-described process is at least 5% bio-based terephthalic acid, meaning that the bio-based terephthalic acid is "isotopically rich" in carbon 14, by at least 5%, as compared to a petroleum source, as determined by ASTM D6866. Preferably, at least 90% of the terephthalic acid is bio-based terephthalic acid, and more preferably, at least 95% of the terephthalic acid is bio-based terephthalic acid.

As also shown in Scheme II above, the bio-based terephthalic acid is converted with methanol to bio-based dimethyl terephthalate selected from the group consisting of bio-based methanol, petroleum based methanol, and combinations thereof to provide the bio-based dimethyl terephthalate. Preferably, the bio-based terephthalic acid is converted to bio-based dimethyl terephthalate of with methanol which is at least 90% bio-based methanol.

In another embodiment of the invention, the bio-based terephthalic acid may be mixed with petroleum based terephthalic acid to make a mixture of bio-based terephthalic acid and petroleum based terephthalic acid. In addition, bio-based dimethyl terephthalate may be mixed with petroleum based dimethyl terephthalate to make a mixture of bio-based dimethyl terephthalate and petroleum based dimethyl terephthalate. These mixtures of bio-based and petroleum based terephthalic acid and dimethyl terephthalate may be subsequently polymerized according to the invention as described herein to make bio-based poly(alkylene terephthalates).

According to another embodiment of the invention, a process of making a compound comprising bio-based 1,4-cyclohexane dimethanol of Formula VII is provided.

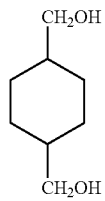

VII

The process comprises providing a biomass comprising a terpene, terpenoid or a mixture thereof. Then, the terpene, terpenoid, or mixture thereof is converted to para-cymene and the para-cymene is converted to bio-terephthalic acid by oxidation, the oxidation being performed in the absence of chromium oxide. The terephthalic acid is then dehydrogenated to produce the bio-based 1,4-cyclohexane dimethanol of Formula VII. According to the invention, at least 5% of the 1,4-cyclohexane dimethanol is bio-based 1,4-cyclohexane dimethanol and the biomass is a biological material which excludes organic material that has been transformed by geological processes into a member selected from the group consisting of petroleum, petrochemicals, and combinations thereof.

As shown in Scheme IV below, bio-based terephthalic acid and bio-based dimethyl terephthalate may be converted by methods known to those of skill in the art, such as a polycondensation reaction, or transesterification, or other methods known to those of skill in the art to produce a variety of bio-based poly(alkylene terephthalate)s of Formula III, also known as polyesters.

Scheme IV

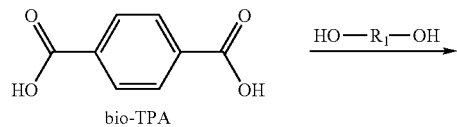

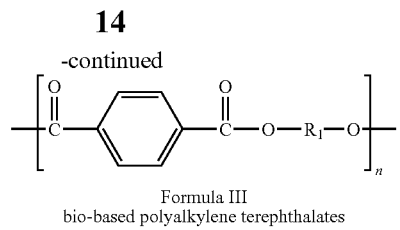

Formula III
bio-based polyalkylene terephthalates

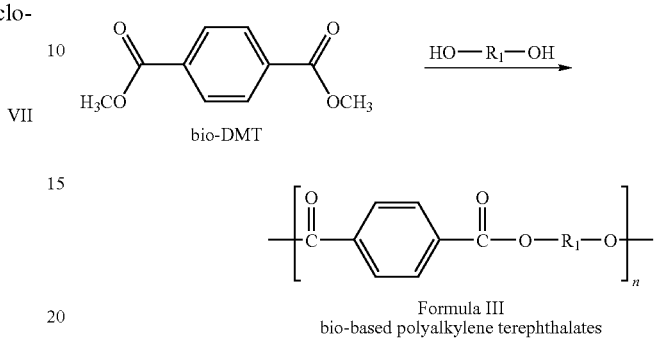

Formula III
bio-based polyalkylene terephthalates

As shown in Scheme IV, the bio-based terephthalic acid and bio-based dimethyl terephthalate are converted to bio-based poly(alkylene terephthalate)s by reaction with a diol of the formula:

HO—$R_1$—OH $R_1$, as shown in Scheme IV above, and also shown in the corresponding diol structure above, is selected from the group consisting of alkyl, cycloalkyl, cycloalkylene alkyl, and cycloalkylene dialkyl groups having from two to ten carbons, and n is an integer between about 50 and about 130. Preferably, the alkyl group is an ethyl, propyl, or butyl group, or a cyclohexylene dimethyl group.

The diol may be petroleum based, bio-based, or a combination thereof. Preferably, the diol of the formula:

HO—$R_1$—OH is at least 80% bio-based.

At least at least 5% of the poly(alkylene terephthalate) is bio-based poly(alkylene terephthalate). Preferably, at least 33% of the poly(alkylene terephthalate) is bio-based poly(alkylene terephthalate). More preferably, at least 80% of the poly(alkylene terephthalate) is bio-based poly(alkylene terephthalate), and most preferably, at least 90% of the poly(alkylene terephthalate) is bio-based poly(alkylene terephthalate).

As shown in Table 1 below, the following poly(alkylene terephthalate)s may be produced according to the process of the invention shown above in Scheme IV from either bio-TPA or bio-DMT, using the diol indicated in Table 1.

TABLE 1

| Formula | Structure | Diol OH—$R_1$—OH | Bio-based Content |
|---|---|---|---|
| IV | 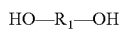<br>bio-based poly(butylene terephthalate) (bio-PBT) | HO—$(CH_2)_4$—OH | At least 5%<br>Preferably at least 60%<br>More preferably at least 80%<br>Most preferably at least 90% |

TABLE 1-continued

| Formula | Structure | Diol OH—R₁—OH | Bio-based Content |
|---|---|---|---|
| V | bio-based poly(trimethylene terephthalate) (bio-PTT) | HO—(CH₂)₃—OH | At least 5% Preferably at least 60% More preferably at least 80% Most preferably at least 90% |
| VI | bio-based poly(ethylene terephthalate) (bio-PET) | HO—(CH₂)₂—OH | At least 5% Preferably at least 60% More preferably at least 80% Most preferably at least 90% |
| VIII | bio-based poly(cyclohexylene dimethyl terephthalate) (bio-PCT) | VII (structure shown) | At least 5% Preferably at least 80% More preferably at least 90% |

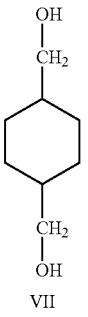

The diol shown in Table 1 above may be bio-based, petroleum based, or a combination thereof. Further, other diol not shown above are within the scope of the invention as will be understood by those of skill in the art by reference to this disclosure.

The invention will be further described by reference to the following non-limiting examples, which are offered to further illustrate various embodiments of the present invention. It should be understood, however, that many variations and modifications can be made while remaining within the scope of the present invention.

EXAMPLES

Example 1

Preparation of Bio-Based Terephthalic Acid from Limonene

Example 1 shows that biologically-derived isotopically rich terephthalic acid was prepared from the terpene, limonene. The method involved two steps, (i) the conversion of limonene to para-cymene and the (ii) conversion of para-cymene to terephthalic acid.

A. Conversion of Limonene to para-cymene.

Referring again to Scheme II, para-cymene, as shown below, was prepared from bio-based limonene as follows.

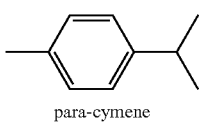

para-cymene

To mixture of ethylenediamine (525 mmol, 31.6 g, 35.2 ml), anhydrous FeCl₃ (0.964 mmol, 0.16 g) and sodium (145 mmol, 3.34 g) was heated to about 50° C. under N₂. After sodium dissolution had started, as evidenced by hydrogen evolution and formation of a dark solution, α-limonene (742 mmol, 101 g, 120 ml), certified as derived from biomass (obtained from Sigma-Aldrich (St. Louis, Mo.), was added dropwise into the mixture and the mixture heated to 100° C. The mixture was heated at 100° C. for 8 h. The mixture was then cooled down and diluted with water (300 ml) and extracted two times with dichloro methane (DCM) (300 ml). The organic layers were dried over magnesium sulfate and concentrated using a rotary evaporator obtaining the crude para-cymene product. Yield: 99% (purity 99%)

B. Conversion of para-Cymene to Bio-based Terephthalic Acid (Formula I).

Referring again to Scheme III, the para-cymene obtained in step A above, was converted to bio-based terephthalic acid of Formula I, shown below, as follows.

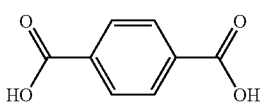

I

The oxidation stage was carried out in two steps as shown in Scheme III. To a solution of the crude of para-cymene product, obtained from the dehydrogenation of α-limonene, (742 mmol, 100 g) in water (400 ml) was added HNO₃ 65% (2968 mmol, 288 g, 206 ml). The reaction mixture was heated to reflux for 1 day and then the mixture was cooled down to room temperature and extracted twice with DCM (400 ml). Then, the organic layers were washed two times with water (100 ml) and concentrated using a rotary evaporator obtaining the crude product.

To the solution of crude product obtained from the oxidation of para-cymene in water (1000 ml) was added NaOH (1484 mmol, 83 g) and the solution was stirred until the solid was dissolved. Potassium permanganate (1484 mmol, 235 g) was then added very slowly. The reaction mixture was heated to reflux for 16 h. The slurry mixture was then filtered on celite pad and washed with water. Concentrated $H_2SO_4$ (98%) was added to the aqueous layer until the pH of solution was strongly acid and all solid was precipitated.

The white solid was filtered, washed with water and DCM (in order to remove the excess of acid and all not completed oxidized products). The resulting pure white solid of bio-based terephthalic acid was dried at 80° C., 50 mmHg for 12 h. Total yield (2 steps): 85%, 105 g.

Note: The dehydrogenation step in step A, that produces para-cymene from limonene was also tested using Pd on charcoal (5% w/w) as a catalyst. The reaction was heated for 6 h at 100° C. under Nitrogen gas, but only a low yield of para-cymene was obtained.

The direct oxidation of p-cymene to terephthalic acid was also attempted using a procedure reported in Ferguson, L. N., et al., *Journal of Organic Chemistry* (1960), 25, 668-70 and a low amount of product was obtained. The best reaction condition were obtained using the two-step procedure described in step B above, comprising first adding concentrated nitric acid to achieve the oxidation of isopropyl moiety then, next, treating this reaction mixture with potassium permanganate to produce the complete oxidation of the intermediate para-cymene products.

C. Determination of the Biological Content of the Bio-based Terephthalic Acid ASTM-D6866 protocol was used to measure the "bio-based content" in a material, in an approach similar to the concept of radiocarbon dating without the use of the age equation. In this approach, the amount of $^{14}C$ in an unknown sample is expressed as a ratio to a modern reference standard. The sample used as a modern reference standard in radiocarbon dating is a standard from NIST (National Institute of Standards and Technology) with a known radiocarbon content equivalent to the year AD 1950. Material from AD 1950 was selected to be "zero years old" because it precedes the thermo-nuclear testing era when large excess of radiocarbon was introduced to the atmosphere. Material from that year is also represented by 100 pMC, Percent Modern Carbon. A fresh biomass such as corn can give a signature of 107.5 pMC, which is higher level of radiocarbon and is directly related to the thermo-nuclear weapon testing that peaked in 1963. To express the results in biomass content, 100% is assigned to equal 107.5 pMC, while 0% is equal to 0 pMC. This result is termed "MEAN BIO-BASED RESULT."

The results reported in this application as MEAN BIO-BASED RESULT include an absolute range of 6% to account for 3% on either side of the MEAN BIO-BASED RESULT to account for variations in end-product radiocarbon signature. All results are based on either bio-based content in "present" material, not amount used in manufacturing process.

Procedure: Bio-based content was determined using ASTM-D6866 method. Samples were first combusted to $CO_2$, quantitatively recovering all carbon species. The $CO_2$ was then reduced in a hydrogen atmosphere over metal catalyst to produce graphite. The graphite was then analyzed in a high sensitivity Mass Spectrometer capable of separating the isotopes carbon-14 and carbon-12. Carbon-14 isotopes were measured as counts in a solid state detector and carbon-12 isotopes were measured as current in a Faraday cup (as microamps). $^{14}C/^{12}C$ ratios were derived for both a modern reference and the sample to derive the bio-based content calculated according to the following equation:

Bio-Based Content=($^{14}C/^{12}C$ ratio sample/$^{14}C/^{12}C$ ratio modern)/1.075

Using the ASTM D6866 test protocols, the MEAN BIO-BASED CONTENT of the bio-based terephthalic acid was 93%.

Example 2

Comparative Example

The method of Example 1.C was practiced, except that ordinary petrochemical-derived terephthalic acid, obtained from Aldrich, was also evaluated for biological carbon content for comparison. Table 2 shows a summary of the results that were obtained from the measuring of the biological content of Examples 1-2.

TABLE 2

| Composition | Source | MEAN BIO-BASED CONTENT, % |
|---|---|---|
| Limonene-derived terephthalic acid | Example 1 | 93% |
| Petrochemical-derived terephthalic acid | Aldrich | 0 |

The results shown in Table 2 confirm that the bio-based terephthalic acid that was derived from limonene was isotopically rich, having a MEAN BIO-BASED CONTENT of at least 93% while the terephthalic acid derived from petrochemical sources did not have any.

Examples 1 and 2 above confirm that the process described herein is an effective way for making biologically derived terephthalic acid from limonene.

Example 3

Bio-based Dimethyl Terephthalate (Formula II)

Referring again to Scheme IV, a synthesis of bio-based dimethyl Terephthalate (Formula II, as shown below) was prepared from bio-based terephthalic acid (Formula I) as follows.

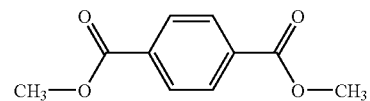

II

To a solution of the bio-based terephthalic acid (632 mmol, 105 g) (obtained in Example 1) in methanol (6320 mmol, 2086 ml) was added concentrated $H_2SO_4$ (31.6 mmol, 3.23 ml) and the mixture was stirred for 1 day at reflux. After cooling down the solution, the solvent was removed and the resulting solid was dissolved in dichloro methane (DCM) (400 ml). The solution was washed with water (200 ml or until pH of solution is neutral), then the organic layer was dried over magnesium sulfate and concentrated using a rotary evaporator to obtain the crude product, a solid. The solid was purified washing it with a small amount of cold methanol and dried at 90° C., for 12 h. The yield that was obtained was 95% (117 g).

Example 4

Comparative Example

The method of Example 3 was practiced, except that ordinary petrochemical-derived dimethyl terephthalate, obtained from Aldrich, was also evaluated for biological carbon content using ASTM 6866 for comparison. Table 2 shows a summary of the results that were obtained.

TABLE 3

| Composition | Source | MEAN BIO-BASED CONTENT, % |
|---|---|---|
| Limonene-derived dimethyl terephthalate | Example 3 | 81% |
| Petrochemical-derived dimethyl terephthalate | Aldrich | 0 |

The results confirm that the isotopically rich dimethyl terephthalate that was derived from limonene had a MEAN BIO-BASED CONTENT of at least 81% while the dimethyl terephthalate from petrochemical sources did not have any. Examples 3 and 4 show that the process described herein is an effective way for making bio-based dimethyl terephthalate (bio-DMT) from limonene.

Example 5

Bio-based Poly(Butylene Terephthalate) (Bio-PBT)

Bio-based poly(butylene terephthalate) (bio-PBT) (Formula IV, as shown below) was prepared from bio-based dimethyl terephthalate (Formula II) as follows.

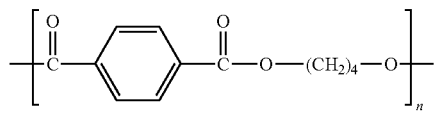

IV

Bio-PBT was made starting from bio-DMT, obtained from limonene (100 mmol, 19.4 g) and 1,4-butanediol (BDO) (160 mmol, 14.4 g) (DMT/BDO=1.6 molar ratio), triisopropyl titanate (TPT), made by Dupont as a tranesterification catalyst (0,027 g, 175 ppm of titanium) was added. The synthesis was carried out with a two-stage polycondensation procedure in a 250 ml round-bottom wide-neck reactor, closed at the top with three-neck flat flange lid equipped with a mechanical stirrer (100-50 rpm).

The lid was heated at a temperature of 90° C. in the first stage and 120° C. in the second stage, with a heating band. A condenser (liquid nitrogen cooled) was connected to the reactor to collect volatile products during the first and the second stage. The reactor was heated by thermostated oil bath in which the system was placed.

In the first stage, conducted at atmospheric pressure, the temperature of oil bath was kept at 180° C., after 10 min at 210° C. for 90 min. In the second stage, the pressure was slowly reduced from atmospheric to less than 1 mbar and the temperature was raised to 245° C. for 60 min. The viscous polymer was pulled out of the reaction mixture.

According to another embodiment of the invention, bio-PBT was made using the above described procedure, but the raw materials were petroleum derived DMT and bio-based BDO. Bio-based BDO can be made from biologically sourced C4 acids such as succnic acid or maleic acid or fumaric acid, etc by hydrogenation.

According to another embodiment of the invention, bio-PBT was made using the above described polymerization procedure, but the raw materials were both bio-based DMT and bio-based BDO in order to increase the green content of PBT to maximum.

Example 6

Comparative Example

The method of Example 5 was practiced, except that ordinary petrochemical-derived PBT, obtained from Sabic Innovative Plastics, USA, was also evaluated for biological carbon content using ASTM 6866 for comparison. Table 4 shows a summary of the results that were obtained.

TABLE 4

| Composition | Source | MEAN BIO-BASED CONTENT, % |
|---|---|---|
| PBT made from Limonene-derived DMT + Petrochemical derived BDO | Example 5 | 66 |
| Petrochemical-derived PBT | Sabic, USA | 0 |
| PBT made from Petrochemical derived DMT + Bio derived BDO | Example 5 | 28 |
| PBT made from Limonene-derived DMT + Bio derived BDO | Example 5 | 94 |

The results confirm that the bio-PBT had a MEAN BIO-BASED CONTENT of at least 28% while the PBT from petrochemical sources (Sabic, USA) did not have any. The experiment confirms that the process described above is an effective way for making bio-based PBT.

Example 7

Bio-based Poly(Ethylene Terephthalate) (Bio-PET)

Bio-based poly(ethylene terephthalate) (bio-PET, Formula V, shown below) was prepared from bio-based dimethyl terephthalate (Formula II) as follows.

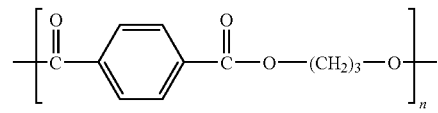

V

Bio-PET was made starting from bio-DMT, obtained from limonene (120 mmol, 23.3 g) and 1,2-ethylene glycol (EG) (264 mmol, 16.4 g) (DMT/EG=2.2 molar ratio), with TPT (0,019 g, 100 ppm of titanium). The synthesis was carried out with a two-stage polycondensation procedure in a 250 ml round-bottom wide-neck reactor, closed at the top with three-neck flat flange lid equipped with a mechanical stirrer (100-50 rpm). The lid was heated at a temperature of 90° C. in the first stage and 120° C. in the second stage, with a heating band. A condenser (liquid nitrogen cooled) was connected to the reactor to collect volatile products during the first and the second stage. The reactor was heated by thermostated oil bath in which the system was placed.

In the first stage, conducted at atmospheric pressure, the temperature of oil bath was kept at 165° C., after 5 min at 210° C. for 160 min. In the second stage, the pressure was slowly reduced from atmospheric to less than 1 mbar and the temperature was raised to 280° C. for 90 min. The viscous polymer was pulled out of the reaction flask.

Example 8

Comparative Example

The method of Example 7 was practiced, except that ordinary petrochemical-derived PET, obtained from Futura Polyesters, Chennai, India, was also evaluated for biological carbon content using ASTM 6866 for comparison. Table 5 shows a summary of the results that were obtained.

TABLE 5

| Composition | Source | MEAN BIO-BASED CONTENT, % |
|---|---|---|
| PET made from Limonene-derived DMT + Petrochemical derived EG | Example 3 | 79 |
| Petrochemical-derived PET | Futura Polyesters, India | 0 |

The results confirm that the bio-PET that was derived from limonene had a MEAN BIO-BASED CONTENT of at least 79%, while the PET from petrochemical sources (Futura Polyesters, India) did not have any. The experiment confirms that the process described above is an effective way for making bio-based PET.

Example 9

Bio-based Poly(Trimethylene Terephthalate) (Bio-PTT)

Bio-based poly(trimethylene terephthalate) (bio-PTT, Formula VI, shown below) was prepared from bio-DMT as follows.

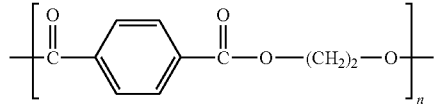

VI

Bio-PTT was made starting from DMT obtained from limonene (100 mmol, 19.4 g) and 1,3-propylene glycol (PDO) (170 mmol, 13.2 g) (DMT/PD=1.7 molar ratio), with TPT (0,015 g, 94 ppm of titanium).

The synthesis was carried out with a two-stage polycondensation procedure in a 250 ml round-bottom wide-neck reactor, closed at the top with three-neck flat flange lid equipped with a mechanical stirrer (100-50 rpm).

The lid was heated at a temperature of 90° C. in the first stage and 120° C. in the second stage, with a heating band. A condenser (liquid nitrogen cooled) was connected to the reactor to collect volatile products during the first and the second stage. The reactor was heated by thermostated oil bath in which the system was placed.

In the first stage, conducted at atmospheric pressure, the temperature of oil bath was kept at 180° C., after 10 min at 205° C. for 90 min. In the second stage, the pressure was slowly reduced from atmospheric to less than 1 mbar and the temperature was raised to 245° C. for 90 min. The viscous polymer was pulled out of the flask.

Example 10

Comparative Example

The method of Example 9 was practiced, except that ordinary petrochemical-derived PTT, obtained from Futura Polyesters, Chennai, India, was also evaluated for biological carbon content using ASTM 6866 for comparison. Table 6 shows a summary of the results that were obtained.

TABLE 6

| Composition | Source | MEAN BIO-BASED CONTENT, % |
|---|---|---|
| PTT made from Limonene-derived DMT + Petrochemical derived PDO | Example 3 | 71 |
| Petrochemical-derived PTT | Futura Polyesters | 0 |

The results confirm that the Bio-PTT that was derived from limonene had a MEAN BIO-BASED CONTENT of at least 71% while the PTT from petrochemical sources (Futura Polyesters, India) did not have any. The experiment confirms that the process described above is an effective way for making bio-based PTT.

Example 11

Bio-based Poly(Cyclohexylene Dimethyl Terephthalate) (Bio-PCT)

Bio-based poly(cyclohexylene dimethyl terephthalate) (bio-PCT, Formula VIII, shown below) was made from bio-DMT as follows.

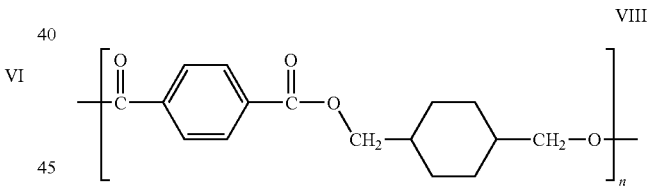

VIII

Bio-PCT was synthesized starting from bio-DMT obtained from limonene (100 mmol, 19.4 g) and 1,6-cyclohexane dimethanol (CHDM) (170 mmol, 13.2 g) (DMT/CHDM=1.7 molar ratio), with TPT (0,015 g, 94 ppm of titanium).

The synthesis was carried out with a two-stage polycondensation procedure in a 250 ml round-bottom wide-neck reactor, closed at the top with three-neck flat flange lid equipped with a mechanical stirrer (100-50 rpm).

The lid was heated at a temperature of 90° C. in the first stage and 120° C. in the second stage, with a heating band. A condenser (liquid nitrogen cooled) was connected to the reactor to collect volatile products during the first and the second stage. The reactor was heated by thermostated oil bath in which the system was placed.

In the first stage, conducted at atmospheric pressure, the temperature of oil bath was kept at 180° C., after 10 min at 205° C. for 90 min. In the second stage, the pressure was slowly reduced from atmospheric to less than 1 mbar and the temperature was raised to 300° C. for 30 min. The viscous polymer was pulled out of the flask.

Example 12

Comparative Example

The method of Example 11 was practiced, except that ordinary petrochemical-derived PCT, obtained from Eastman, USA, was also evaluated for biological carbon content using ASTM 6866 for comparison. Table 7 shows a summary of the results that were obtained.

TABLE 7

| Composition | Source | MEAN BIO-BASED CONTENT, % |
|---|---|---|
| PCT made from Limonene-derived DMT + Petrochemical derived CHDM | Example 3 | 49 |
| Petrochemical-derived PCT | Eastman | 0 |

The results confirm that the bio-PCT that was derived from limonene had a MEAN BIO-BASED CONTENT of at least 49% while the PCT from petrochemical sources (Eastman, USA) did not have any. The experiment confirms that the process described above is an effective way for making bio-based PCT.

Example 13

Bio-based Polymer Characterization

The poly(alkylene terephthalates) prepared and/or analyzed in the above Examples 5-9 were analyzed and characterized according to known methods, or the information below was obtained from the manufacturer specifications. The comparative results are shown in Table 8 below.

TABLE 8

General characterization of Polyesters.

| | GPC | | | TGA | | DSC | | |
|---|---|---|---|---|---|---|---|---|
| | $M_w$ | $M_n$ | PDI | $T_{peak}$ (° C.) | $T_{onset}$ (° C.) | $T_g$ (° C.) | $T_m$ (° C.) | $T_c$ (° C.) |
| bio-PBT (Example 5) | 113000 | 46700 | 2.4 | 415 | 395 | — | 222 | 181 |
| PBT 195 (Example 6) | 57000 | 28000 | 2.1 | 413 | 392 | — | 223 | 174 |
| bio-PET (Example 7) | 93000 | 38000 | 2.4 | 452 | 423 | 82 | 251 | 174 |
| PET (Example 8) | 62000 | 30000 | 2.0 | 451 | 426 | 84 | 257 | 192 |
| PTT (Example 9) | 70000 | 32000 | 2.2 | 413 | 390 | — | 230 | 158 |

The data in Table 8 shows that the poly(terephthalates) prepared according to the invention have similar properties and thus similarly applicable applications, such as in fabrics, blow molded plastics, and other uses.

Although the present invention has been discussed in considerable detail with reference to certain preferred embodiments, other embodiments are possible. Therefore, the scope of the appended claims should not be limited to the description of preferred embodiments contained herein.

What is claimed is:

1. A process of making a bio-based terephthalic acid composition, the process comprising:
   (a) providing a biomass comprising limonene;
   (b) converting the limonene to para-cymene at a yield of at least 95%; and
   (c) converting the para-cymene to terephthalic acid at a total yield of at least 85% by oxidation in a two-step oxidation comprising:
      (i) a first step using a mineral acid, and
      (ii) a second step using a transition metal oxidant,
   the oxidation being performed substantially in the absence of chromium oxide;
   wherein the bio-based terephthalic acid has a mean bio-based content of at least 95%;
   and wherein the biomass is a biological material which excludes organic material that has been transformed by geological processes into a member selected from the group consisting of petroleum, petrochemicals, and combinations thereof.

2. A process according to claim 1 wherein the transition metal oxidant is a permanganate compound.

3. A process according to claim 1 wherein the limonene is converted to para-cymene in the presence of a catalyst selected from the group consisting of metal catalysts, amine catalysts, and combinations thereof.

4. A process according to claim 1 wherein the limonene is converted to para-cymene in the presence of a catalyst selected from the group consisting of transition metal catalysts, Group IA catalysts, amine catalysts, and combinations thereof.

5. A process of making bio-based dimethyl terephthalate of Formula II:

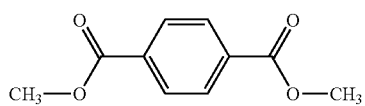

II the process comprising:
   (a) providing a biomass comprising limonene;
   (b) converting limonene to bio-based para-cymene at a yield of at least 95%;
   (c) converting the bio-based para-cymene to bio-based terephthalic acid of Formula I: at a total yield of at least 85%

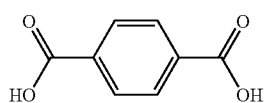

I by an oxidation in a two-step oxidation comprising:
   (i) a first step using a mineral acid, and
   (ii) a second step using a transition metal oxidant,
performed substantially in the absence of chromium oxide; and
   (d) converting the bio-based terephthalic acid with methanol selected from the group consisting of bio-based methanol, petroleum based methanol, and combinations thereof to provide the bio-based dimethyl terephthalate of Formula II, wherein the bio-based terephthalic acid has a mean bio-based content of at least 5%; and wherein the biomass is a biological material which excludes organic material that has been transformed by geological processes into a member selected from the group consisting of petroleum, petrochemicals, and combinations thereof.

6. A process according to claim 5 wherein the bio-based terephthalic acid is converted to bio-based dimethyl terephthalate of Formula II with bio-based methanol, the bio-based methanol having a mean bio-based content of at least 90%.

7. A process according to claim 6 further comprising mixing the bio-based terephthalic acid of Formula (I) with petroleum based terephthalic acid to make a mixture of bio-based terephthalic acid and petroleum based terephthalic acid.

8. The process of claim 5 wherein the mineral acid is nitric acid.

9. The process of claim 1 wherein the first step comprises obtaining an oxidized product that is directly extracted using an organic layer.

10. The process of claim 1 wherein the first step comprises heating the p-cymene with water and mineral acid to obtain an oxidized product, which that is then cooled down, extracted with organic solvent, concentrated, dissolved in water, and further oxidized with the transition metal oxidant to obtain bio-based terephthalic acid.

11. The process of claim 10 wherein the concentrated oxidized product is dissolved in water with sodium hydroxide.

12. A process of making a bio-based terephthalic acid composition, the process comprising:
(a) providing a biomass comprising limonene;
(b) converting the limonene to para-cymene at a yield of at least 95%; and
(c) converting the para-cymene to terephthalic acid at a total yield of at least 85% by oxidation in a two-step oxidation comprising:
(i) a first step, using a mineral acid, comprising heating a reaction mixture comprising p-cymene, mineral acid, and water, which reaction mixture is then cooled down and extracted with organic solvent; and
(ii) a second step using a transition metal oxidant, and oxidized with the oxidant to obtain bio-based terephthalic acid;

wherein the oxidation is performed substantially in the absence of chromium oxide;

wherein the bio-based terephthalic acid has a mean bio-based content of at least 95%; and wherein the biomass is a biological material which excludes organic material that has been transformed by geological processes into a member selected from the group consisting of petroleum, petrochemicals, and combinations thereof.

* * * * *